(12) United States Patent
Kataw

(10) Patent No.: US 8,345,906 B1
(45) Date of Patent: Jan. 1, 2013

(54) EAR PLUG HAVING AN ADJUSTABLE SHAFT

(76) Inventor: Kaled Kataw, West Milford, NJ (US)

( * ) Notice: Subject to any disclaimer, the term of this patent is extended or adjusted under 35 U.S.C. 154(b) by 1240 days.

(21) Appl. No.: 11/446,807

(22) Filed: Jun. 3, 2006

(51) Int. Cl.
H04R 25/00 (2006.01)
A61B 7/02 (2006.01)
(52) U.S. Cl. ............................... 381/328; 181/135
(58) Field of Classification Search ............... 381/380, 381/328, 312–318
See application file for complete search history.

(56) References Cited

U.S. PATENT DOCUMENTS

| 3,800,791 | A | * | 4/1974 | Visor | 128/864 |
| 6,938,622 | B2 | * | 9/2005 | Huang | 181/135 |
| 2005/0087195 | A1 | * | 4/2005 | Huang | 128/864 |

* cited by examiner

Primary Examiner — Curtis Kuntz
Assistant Examiner — Sunita Joshi
(74) Attorney, Agent, or Firm — Arthur I. Degenholtz

(57) ABSTRACT

An ear plug has a body member, an insert member and a shaft member. The body member has a central bore and the insert member projects into the central bore. A portion of the shaft member is threaded into the insert member and a portion of the shaft member bears against a portion of the bore. Rotation of the shaft relative to the insert causes an enlarged portion of the shaft to bear against the bore of the body member which is flexible and forces the body member to flex outwardly and to bear against the user's ear canal forming a seal against entry of water into the user's ear.

16 Claims, 5 Drawing Sheets

EAR PLUG HAVING AN ADJUSTABLE SHAFT

FIELD OF THE INVENTION

The present invention relates generally to the field of ear plugs and more particularly to an ear plug having an adjustable shaft for use during swimming to prevent entry of water into the ear.

BACKGROUND OF THE INVENTION

The prior art related to ear plugs includes the following United States patents.

U.S. Pat. No. 2,053,995 to Hoey shows a device with a threaded shaft which can be rotated using the projections formed on an inner shaft to expand a hollow body. The hollow body is expanded to create a seal against the ear canal when the device is shortened using a threaded shaft which is attached to the end of the hollow body.

U.S. Pat. No. 2,888,921 to Nielson et al. shows a balloon-like member which fills the ear canal. The balloon-like member is pressurized slightly above normal atmospheric pressure and a tubular member aids in the insertion of the balloon-like member into the ear. The internal pressure in the balloon-like member creates a seal against the ear canal.

U.S. Pat. No. 3,783,864 to Moller shows a flexible member which can be expanded to fit the ear canal by rotation of a nut. The device includes a hollow tube for transmission of sound.

U.S. Pat. No. 3,123,069 to Laisne et al. shows a plunger which acts to change the diameter of a hollow member to allow insertion and to provide a close fit in the ear canal. The plunger is attached to the end of the hollow member. The plunger serves to elongate the hollow member thereby reducing the diameter for insertion into the ear canal.

U.S. Pat. No. 3,800,791 to Visor shows a device in which a threaded insert is rotated and is thereby forced into a cavity in an ear plug resulting in the increase in the diameter of a flexible flange to create a seal in the ear canal.

U.S. Pat. No. 6,830,124 B2 and 2004/0211621 A1 to Chaing shows a device which incorporates an integral handle for insertion and removal of the device. The device relies on the flexibility of flange-like members to create a seal.

Despite the various developments in the prior art, there remains a need for an ear plug with an adjustable shaft which combines ease of use with a high degree of retention in the user's ear with effective sealing against entry of water into the user's ear canal.

OBJECTS AND SUMMARY OF THE INVENTION

It is an object of the present invention to provide an ear plug having an adjustable shaft which can be easily inserted into the ear of a user to prevent entry of water during swimming.

Another object of the present invention is to provide an ear plug having an adjustable shaft which can be easily adjusted to bear against the surface of the ear canal to accommodate anatomical differences in ear canal sizes between different users.

Another object of the present invention is to provide an ear plug having an adjustable shaft which can be easily adjusted to ensure secure retention in the ear canal during use.

Another object of the present invention is to provide an ear plug having an adjustable shaft which can be easily removed after use.

Another object of the present invention is to provide an earplug having an adjustable shaft which can provide reliable long term operation.

Yet another object of the present invention is to provide an ear plug with an adjustable shaft which comprises a small number of component parts which can be manufactured economically in volume resulting in a relatively low unit cost.

Other objects and advantages of the present invention will be made clear hereinafter.

In accordance with the present invention there is provided an ear plug having an adjustable shaft for use by swimmers which includes a flexible body member, a shaft member and an insert member. The body member has a central bore and the insert projects into the central bore. A portion of the shaft member is threaded into the insert member. An enlarged portion of the shaft bears against a portion of the bore. The end of the body member is relatively soft which facilitates easy insertion into the ear canal. Rotating the shaft relative to the insert causes the enlarged portion of the shaft to bear against the bore of the body member and forces the body member to flex outwardly against the user's ear canal forming an effective seal against entry of water into the user's ear.

Other important objects and advantages of the present invention will be apparent from the following detailed description of the invention taken in connection with the accompanying drawings in which:

DETAILED DESCRIPTION OF THE INVENTION

Figure 1:
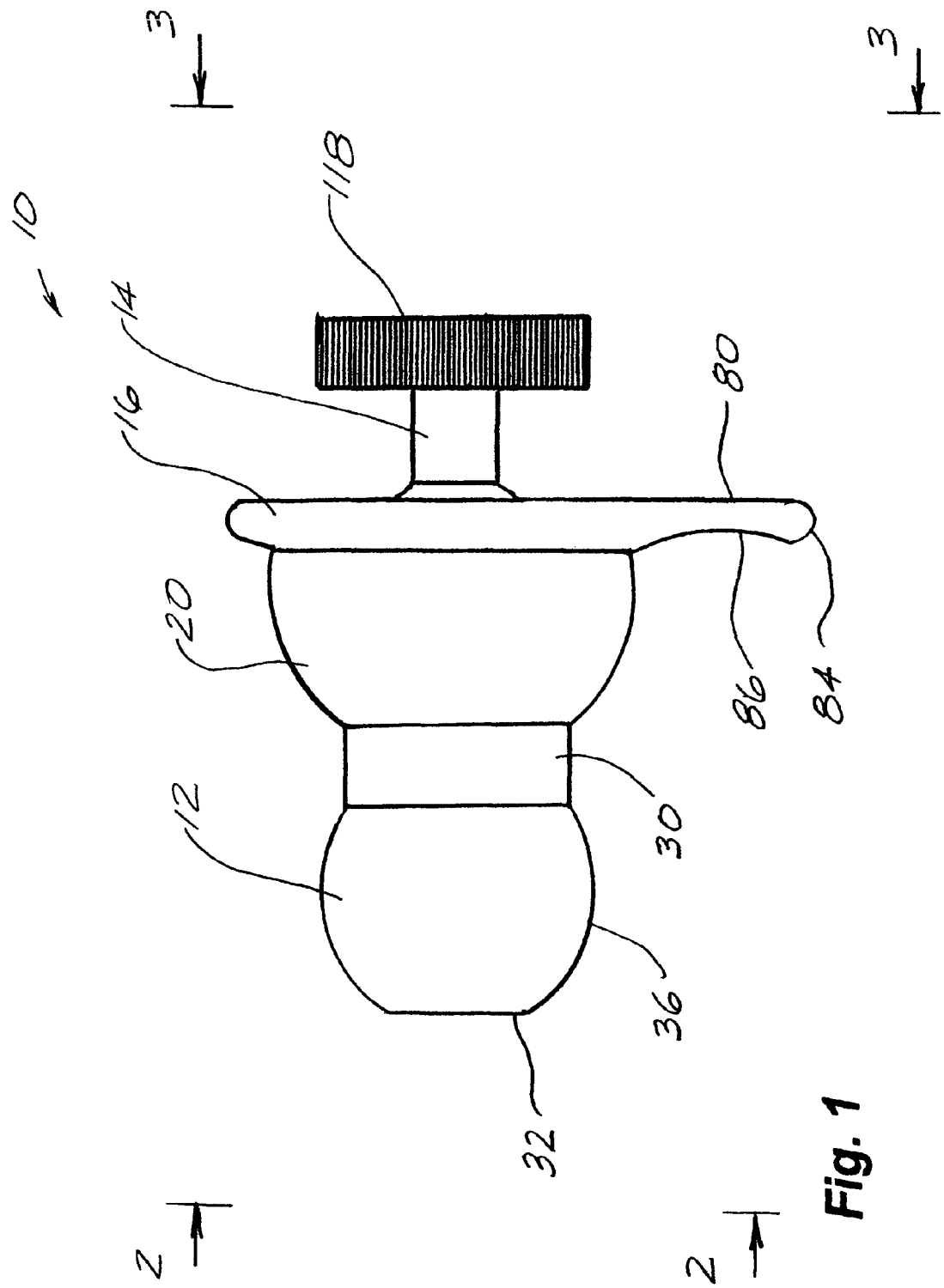
FIG. 1 is a side elevation view of an ear plug made in accordance with the present invention.
Figure 2:
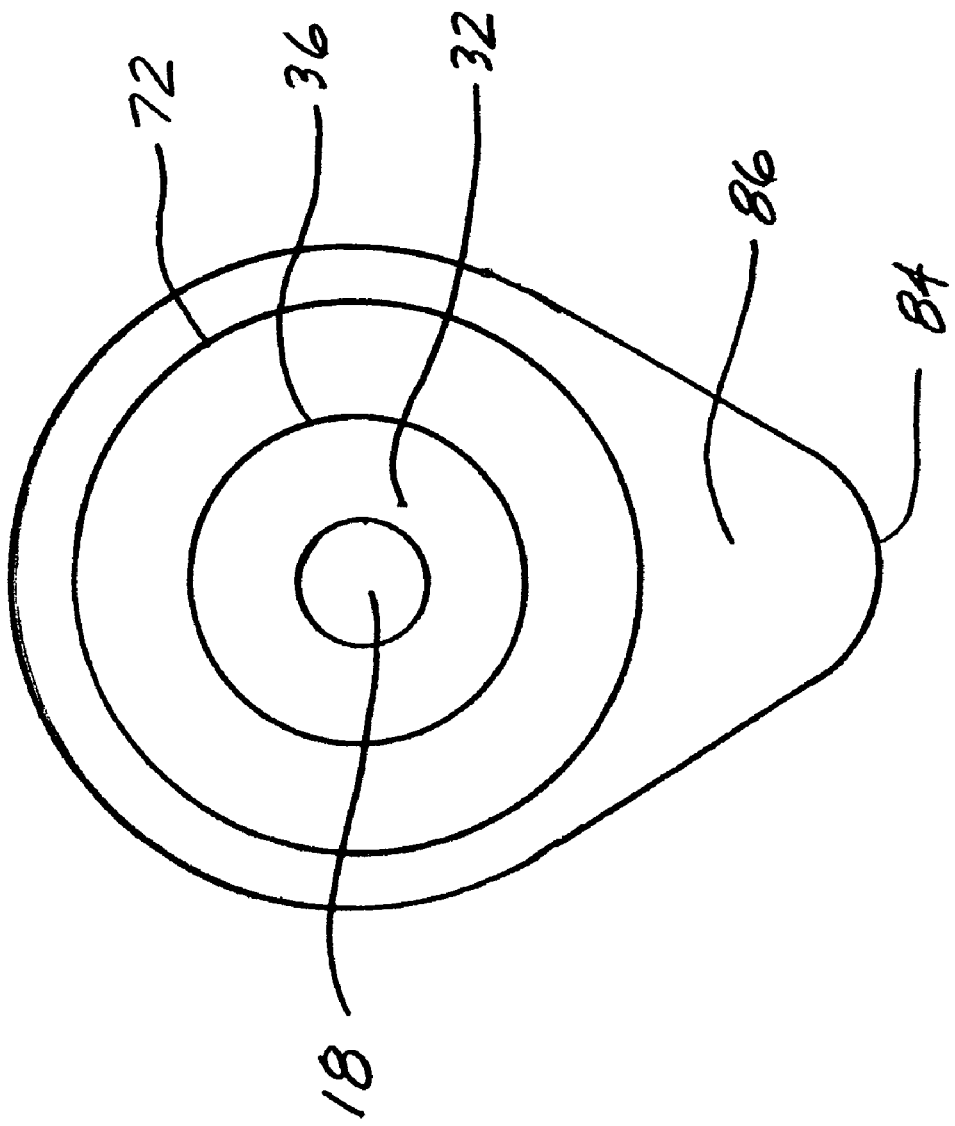
FIG. 2 is an end elevation view taken along the line 2-2 of FIG. 1.
Figure 3:
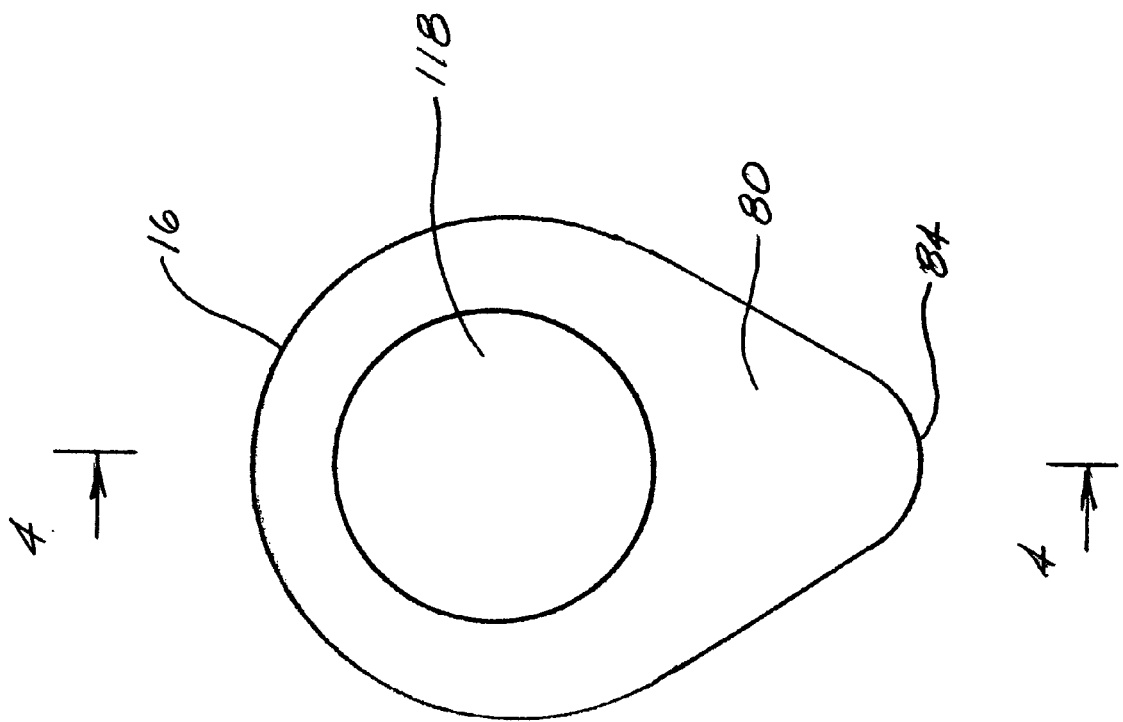
FIG. 3 is an end view taken along the line 3-3 of FIG. 3.

With reference to the drawings there is shown in FIGS. 1-5 an ear plug having an adjustable shaft 10 for use by swimmers, made in accordance with the present invention, which includes a body member 12, a shaft member 14 and an insert member 16.

The body member 12 is a unitary member which has a central bore 18 into which the insert member 16 and the shaft member 14 project. The outer surface 20 of the body member 12 has a first portion 22 which has a generally convex curvature having an area of relatively larger diameter 24 and an area of relatively smaller diameter 26. The relatively smaller diameter 26 leads to a second portion 28 which has a generally cylindrical surface 30.

The end 32 of the second portion 28 leads to a third portion 34 which has a surface 36 which has a convex curvature. The end portion 32 of the third portion 34 is convexly rounded. The central bore 18 of the body member 12 defines the fourth portion 42 of the body member 12. The surface 40 has a first area 44 which is generally concave and which extends inwardly from the end portion 32. The first area 44 of the bore 18 and the third portion 34 together define an area 46 of the body member 12 in which the wall thickness of the body member 12 is generally uniform. The area 44 is inwardly curved and is generally flexible A second area 48, which is generally conical, extends inwardly from the first area 44. The second area 48 defines an area 50 of increasing wall thickness with a relatively thinner portion 52 forming a smooth transition from the area 46 of generally uniform thickness and with a relatively thicker portion 54 which is spaced away from the outer end 32. The generally conical surface 48 forms a key feature of the present invention as will presently be described. The conical surface 48 leads to a surface 56 which is generally cylindrical.

Figure 4:
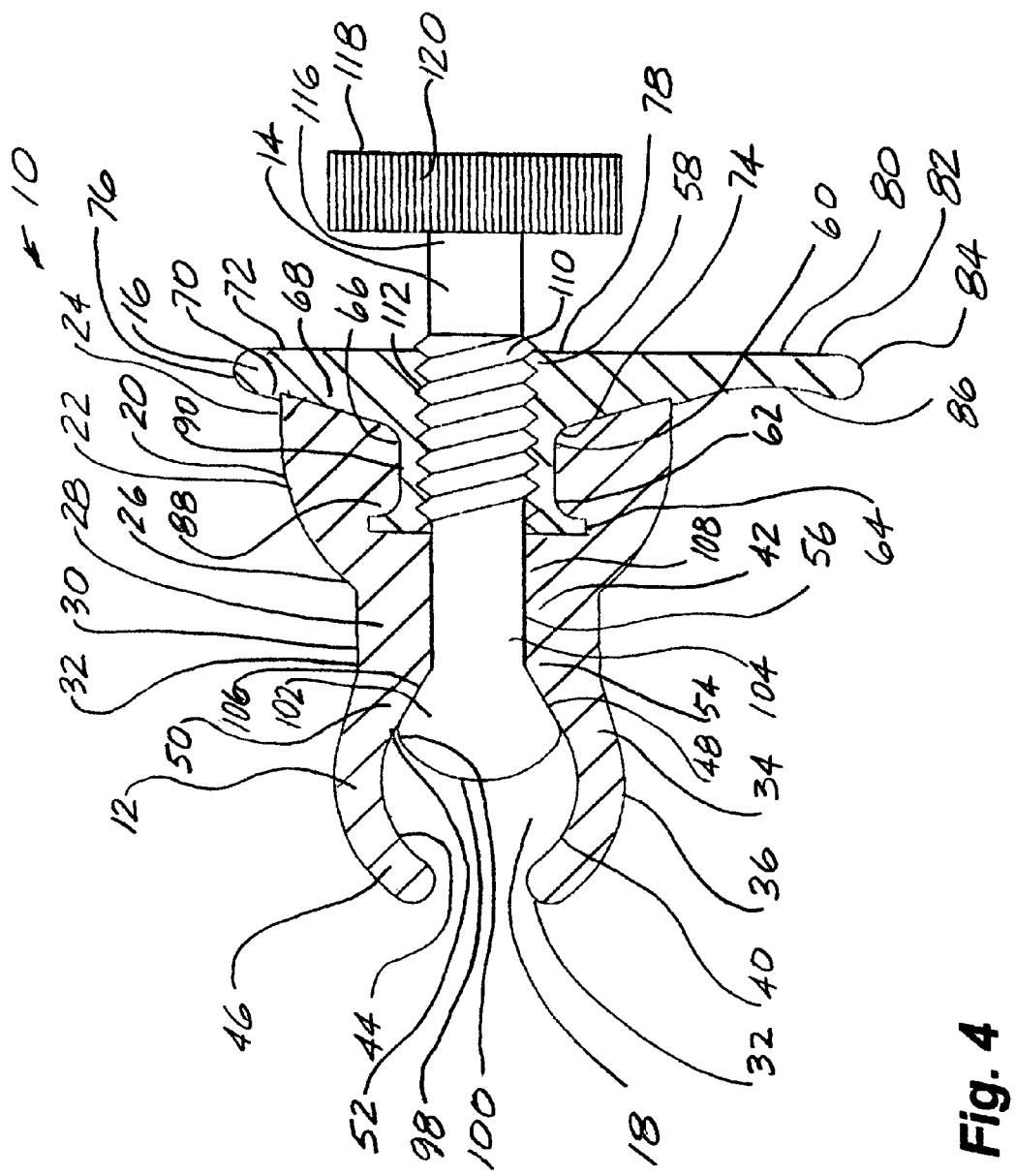
FIG. 4 is a cross-sectional view taken along the line 4-4 of FIG. 2.

As is best shown in FIG. 4, the insert member 16 is a unitary member which has a central bore 58 which is threaded. Surrounding the central bore 58 there is a generally cylindrical portion 60 the first end 62 of which has an outwardly flared flange portion 64.

The second end 66 of the cylindrical portion 60 leads to an outwardly flared portion 68 which has an integrally formed lip portion 70 and a flat end surface 72. A curved transitional area 74 connects the cylindrical portion 60 and the outwardly flared portion 68. The outwardly flared portion 68 has a rounded outer edge portion 76.

A grip portion 80 having an elongated portion 82 projects from the outwardly flared portion 68 as is best shown in FIG. 4. The grip portion 80 has a convexly curved end portion 84 and a concave portion 86 which are blended to form a smooth transition. The grip portion 80 can be easily grasped by the user's fingers.

The body member 12 has an internal surface contour 88, which complements and closely fits the surface portion contour 90 of the insert member 16.

The shaft member 14 has an enlarged first end 98 which is convexly curved and which has a curved transition portion 100 which leads to an inwardly flared conical portion 102 which in turn leads to a cylindrical portion 104.

The conical portion 102 of the shaft member 14 closely fits the portion 106 of the body member 12 and the cylindrical portion 104 of the shaft member 14 closely fits the portion 108 of the body member 12.

The shaft member 14 has a threaded portion 110 which is threaded into the threaded portion 112 which is formed in the insert member 16. The end 116 of the shaft member 14 has a knob 118 the outer surface of which advantageously has a serrated or knurled surface 120.

The body member 12 is preferably made of a soft rubber-like material such as a nontoxic silicone rubber. The shaft member 14 and the insert member 16 are preferably made of a relatively hard rubber or plastic material.

Figure 5:
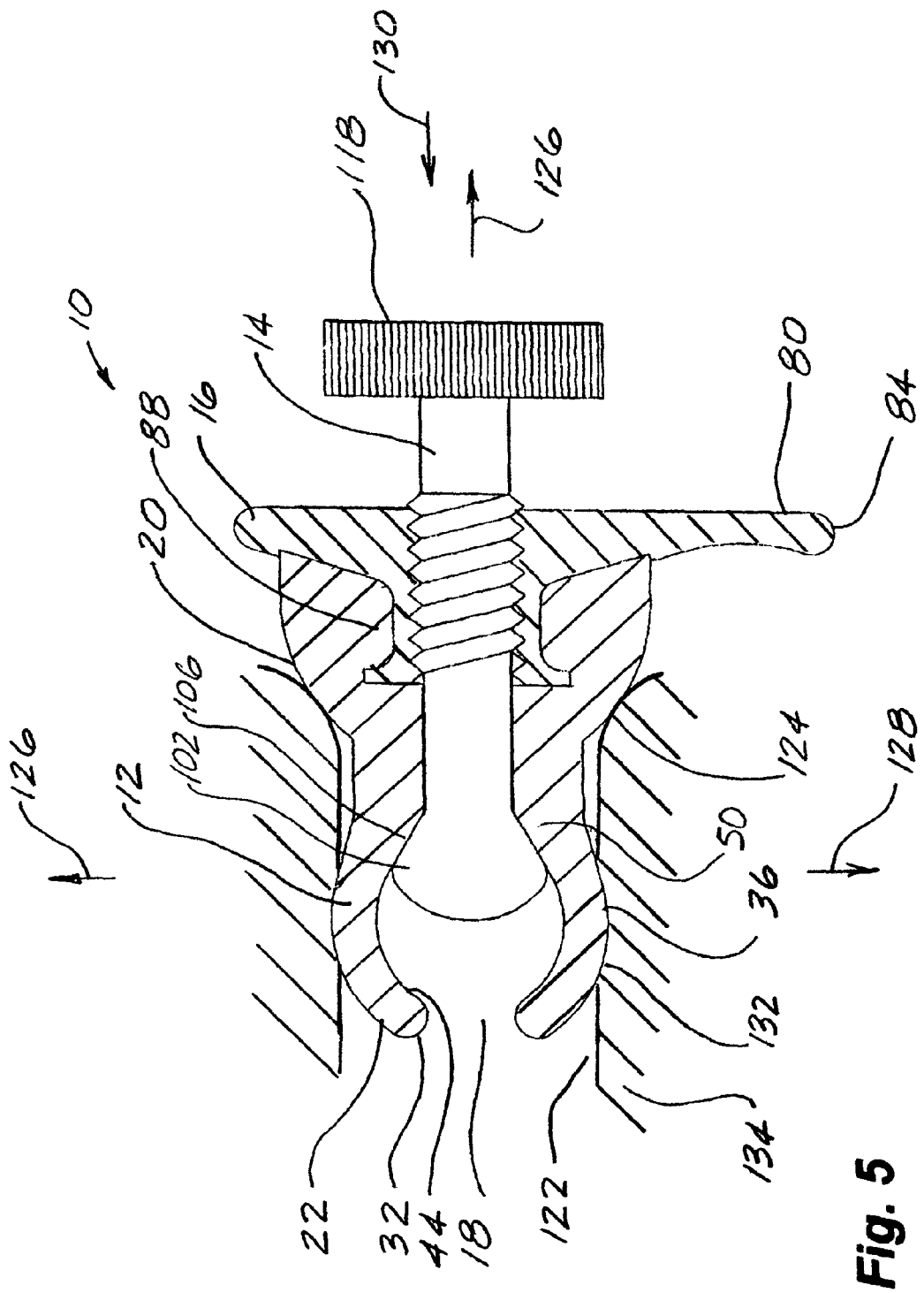
FIG. 5 is a schematic cross-sectional view similar to FIG. 4 showing a portion of the user's ear canal.

During use, the shaft member 14, the insert member 16 and the body member 12 are initially in the position shown in FIG. 4. The normal position of the body member 12 is shown in FIG. 4. The end 32 of the body member 12 is inserted into the ear canal 122 as is shown in FIG. 5. The curved configuration of the rounded end 32 and the relatively thin and flexible wall area 44 provide a relatively soft and compliant structure which facilitates easy insertion into the ear canal 122 without unwanted pain or discomfort.

When the ear plug 10 is inserted into the ear canal 122 the surface 20 acts as a stop when it comes into contact with the surface 124 of the user's ear, preventing excessive insertion, as is shown in FIG. 5. The knob 118 is then rotated relative to the insert member 16 and the body member 12 in a direction to withdraw the shaft 14 from the insert member 16.

The grip portion 80 enables the user to easily hold the insert member 16 while rotating the shaft member 14. As the shaft member 14 moves in the direction shown by the arrow 126 in FIG. 5, the area 102 of the shaft member 14 bears against the surface 106 of the body member 12 thereby causing the body member 12 to flex outwardly and consequently causes the surface 36 to bear against the surface 132 of the ear canal 122 thereby forming an effective seal.

The portion 102 of the shaft member 14 continues to bear against the portion 50 of the body member 12 forming a seal. The ear plug 10 thus effectively prevents water from reaching the inner structure of the user's ear 134.

As shown in FIG. 5 the ear plug 10 presents a surface 36 to the ear canal 122 which is both convexly curved and relatively soft and compliant. This curved and compliant surface 36 enables both the ear canal 122 and the surface 36 to deflect slightly without causing discomfort to the user. As a result of this mutual deflection of both the ear canal 122 and the ear plug 10, the ear plug 10 forms an effective seal against entry of water and the ear plug 10 is also retained securely in the ear canal 122 preventing dislodgement and loss during swimming activities.

When it is desired to remove the ear plug 10 from the ear canal 122 the shaft member 14 is rotated in a direction to drive the shaft member 14 into the insert member 16 in the direction shown by the arrow 130. This causes the portion 102 of the shaft member 14 to cease bearing against the conical portion 106 of the body member 12 and move away from the body member 12 allowing the body member 12 to return to the unflexed state and consequently removing pressure from the ear canal 122.

The portion 88 of the body member 12 is securely fitted against and is securely retained by the lip portion 70, the flared portion 68, the cylindrical portion 90 and the flange portion 64 of the insert member 16 thereby locking the body member 12 and the insert member 16 together and forming a seal.

The foregoing specific embodiment of the present invention as set forth in the specification herein is for illustrative purposes only. Various deviations and modifications may be made within the spirit and scope of the invention without departing from the main theme thereof.

I claim:

1. An ear plug having an adjustable shaft comprising:
   a flexible body member having a central bore, with said central bore having an inner wall portion and an outer wall portion;
   an insert member disposed projecting into said central bore and having a threaded cavity, and
   a shaft member having a threaded portion and an enlarged end portion, with said threaded portion of said shaft member engaged in said threaded cavity of said insert member and with said enlarged end portion of said shaft member bearing against said wall portion of said central bore of said flexible body member and with said enlarged end portion outwardly flaring and whereby rotation of said shaft relative to said flexible body member forces expansion of said outer wall portion wherein said insert member further comprises a flanged portion projecting beyond said outer wall portion of said flexible body member.

2. An ear plug having an adjustable shaft as claimed in claim 1 wherein said shaft member further comprises:
   a knob.

3. An ear plug having an adjustable shaft as claimed in claim 1 wherein said enlarged portion of said shaft member comprises:
   a conical portion.

4. An ear plug having an adjustable shaft as claimed in claim 1 wherein said central bore of said flexible body member comprises:
   a conical portion.

5. An ear plug having an adjustable shaft as claimed in claim 1 wherein said flexible body member further comprises:
   a first convex portion.

6. An ear plug having an adjustable shaft as claimed in claim 1 wherein said flexible body member further comprises:
   a first convex portion and wherein said first convex portion comprises:
   a hollow portion.

7. An ear plug having an adjustable shaft as claimed in claim 6 wherein said first convex portion comprises:
   a rounded end portion.

8. An ear plug having an adjustable shaft as claimed in claim 6 wherein said enlarged end portion end portion of said shaft member bears against said hollow portion of said flexible body member.

9. An ear plug having an adjustable shaft as claimed in claim 1 wherein said insert member comprises:
   a grip portion.

10. An ear plug having an adjustable shaft as claimed in claim 1 wherein said grip portion comprises:
    a projecting portion.

11. An ear plug having an adjustable shaft as claimed in claim 1 wherein said body member is made of a soft flexible rubber.

12. An ear plug having an adjustable shaft as claimed in claim 1 wherein said body member is made of a silicone rubber.

13. An ear plug having an adjustable shaft as claimed in claim 1 wherein said shaft member is made of a plastic material.

14. An ear plug having an adjustable shaft as claimed in claim 1 wherein said body member comprises:
    a second convex portion.

15. An ear plug having an adjustable shaft as claimed in claim 1 wherein said body member comprises:
    a generally cylindrical portion disposed between said first and said second convex portions.

16. An ear plug having an adjustable shaft as claimed in claim 4 wherein rotation of said shaft member relative to said insert member causes said conical portion of said shaft member to bear against said conical portion of said flexible body member.

* * * * *